(12) United States Patent
Underbrink

(10) Patent No.: US 8,009,507 B2
(45) Date of Patent: Aug. 30, 2011

(54) SYSTEM AND METHOD FOR ADAPTABLE APERTURE PLANAR PHASED ARRAY

(75) Inventor: James R. Underbrink, Seattle, WA (US)

(73) Assignee: The Boeing Company, Chicago, IL (US)

( * ) Notice: Subject to any disclaimer, the term of this patent is extended or adjusted under 35 U.S.C. 154(b) by 415 days.

(21) Appl. No.: 12/351,345

(22) Filed: Jan. 9, 2009

(65) Prior Publication Data

US 2010/0175474 A1    Jul. 15, 2010

(51) Int. Cl.
*G03H 3/00* (2006.01)
(52) U.S. Cl. .................. 367/8; 367/7; 367/12; 367/118; 342/367; 381/92
(58) Field of Classification Search .................. 367/7–8, 367/12, 118–121, 124–127, 128, 901; 342/350, 342/367–368, 371; 381/92; 73/583
See application file for complete search history.

(56) References Cited

U.S. PATENT DOCUMENTS

| | | | | |
|---|---|---|---|---|
| 4,176,339 A | * | 11/1979 | Konrad | 367/121 |
| 4,180,814 A | * | 12/1979 | Barton | 342/196 |
| 5,657,295 A | * | 8/1997 | Howard | 367/140 |
| 5,831,936 A | * | 11/1998 | Zlotnick et al. | 367/124 |
| 5,838,284 A | * | 11/1998 | Dougherty | 343/893 |
| 6,205,224 B1 | | 3/2001 | Underbrink | |
| 6,310,831 B1 | * | 10/2001 | Dillman | 367/105 |
| 6,583,768 B1 | | 6/2003 | Underbrink | |
| 6,897,829 B2 | * | 5/2005 | Oliver et al. | 343/893 |
| 7,098,865 B2 | * | 8/2006 | Christensen et al. | 343/893 |
| 7,109,918 B1 | * | 9/2006 | Meadows et al. | 342/368 |
| 7,266,044 B2 | * | 9/2007 | Yang | 367/124 |
| 2003/0076274 A1 | | 4/2003 | Phelan et al. | |
| 2006/0256659 A1 | * | 11/2006 | Turgut | 367/123 |
| 2006/0256975 A1 | * | 11/2006 | Brooks et al. | 381/92 |
| 2006/0284768 A1 | * | 12/2006 | Pauplis | 342/368 |

OTHER PUBLICATIONS

Haykin, S.; Reilly, J.P.; Kezys, V.; Vertatschitsch, E., "Some aspects of array signal processing", Radar and Signal Processing, IEE Proceedings F (0956-375X), 1992.vol. 139,Iss.1;p. 1-26.*

Sachar, J.M.; Silverman, H.F.; Patterson, W.R., "Microphone position and gain calibration for a large-aperture microphone array", Speech and Audio Processing, IEEE Transactions on (1063-6676), 2005.vol. 13,Iss.1; p. 42-52.*

(Continued)

*Primary Examiner* — Isam Alsomiri
*Assistant Examiner* — James Hulka
(74) *Attorney, Agent, or Firm* — Harness, Dickey & Pierce, P.L.C.

(57) ABSTRACT

A system for an adaptable aperture planar array for maintaining source resolution is provided. The system includes a first nested array defining a first aperture responsive to a first range of frequencies. The first aperture is sized based on an angle between the array and the source, and includes a first subset of sensor elements. The system includes a second nested array defining a second aperture responsive to a second range of frequencies that is less than the first range of frequencies. The second aperture is sized based on the angle between the array and the source, and includes a second subset of sensor elements. The first aperture and second aperture change in size as the angle changes, which results in a change in the sensor elements within the first subset and the second subset to maintain the source resolution for the array.

21 Claims, 11 Drawing Sheets

OTHER PUBLICATIONS

Cardone, G.; Cincotti, G.; Gori, P.; Pappalardo, M., "Optimization of wide-band linear arrays", Ultrasonics, Ferroelectrics and Frequency Control, IEEE Transactions on (0885-3010), 2001.vol. 48,Iss.4; p. 943-952.*

* cited by examiner

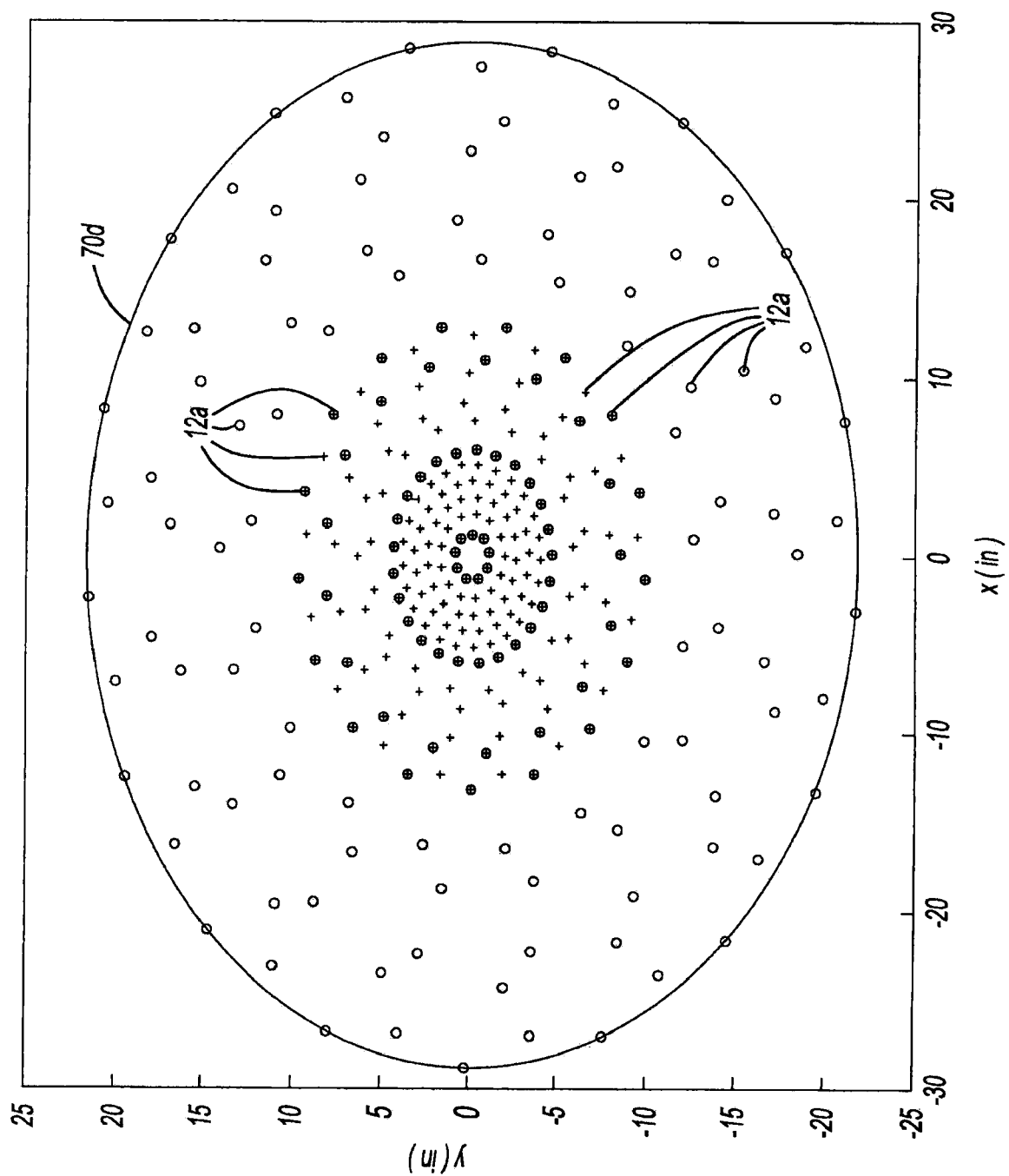

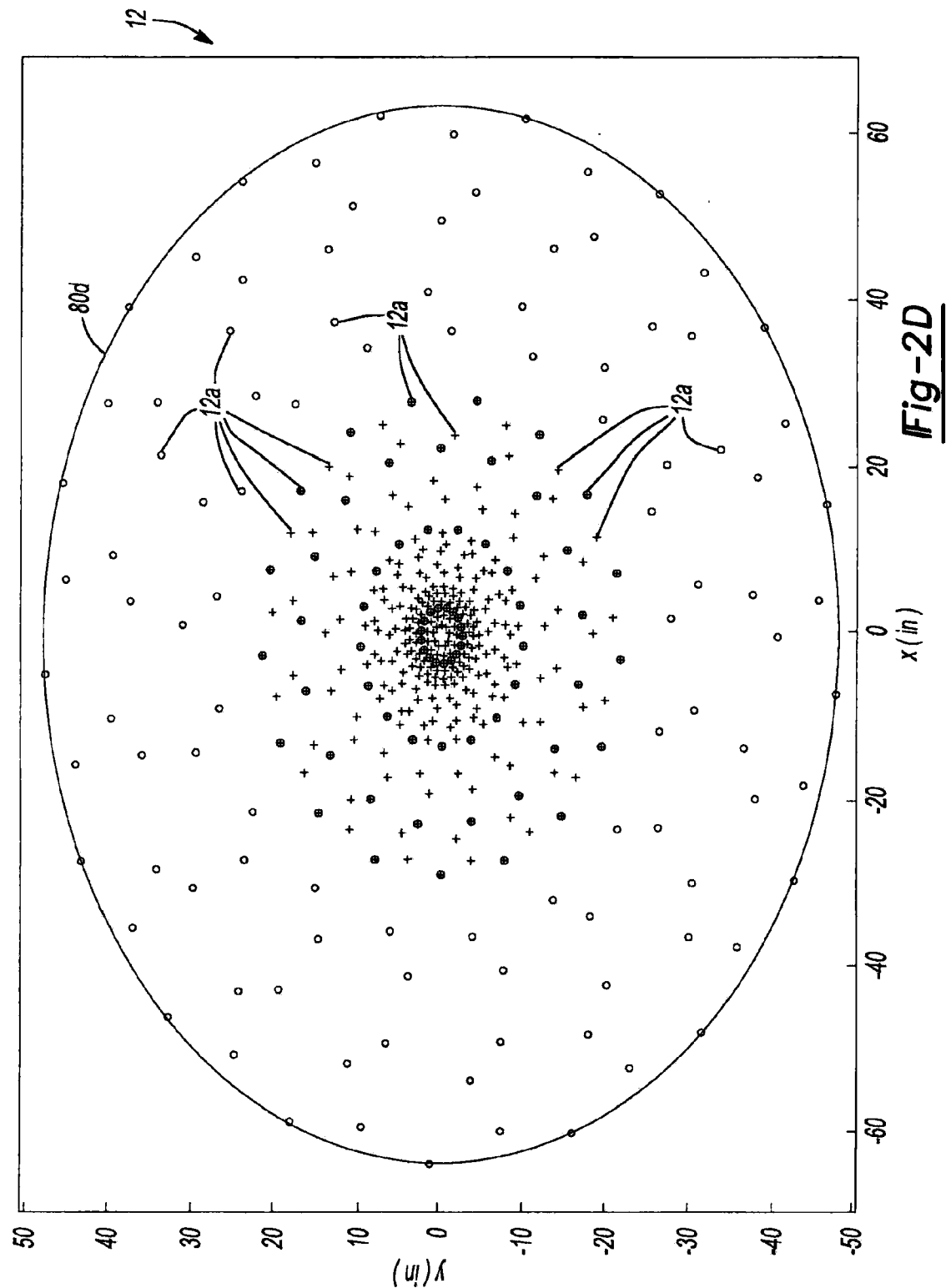

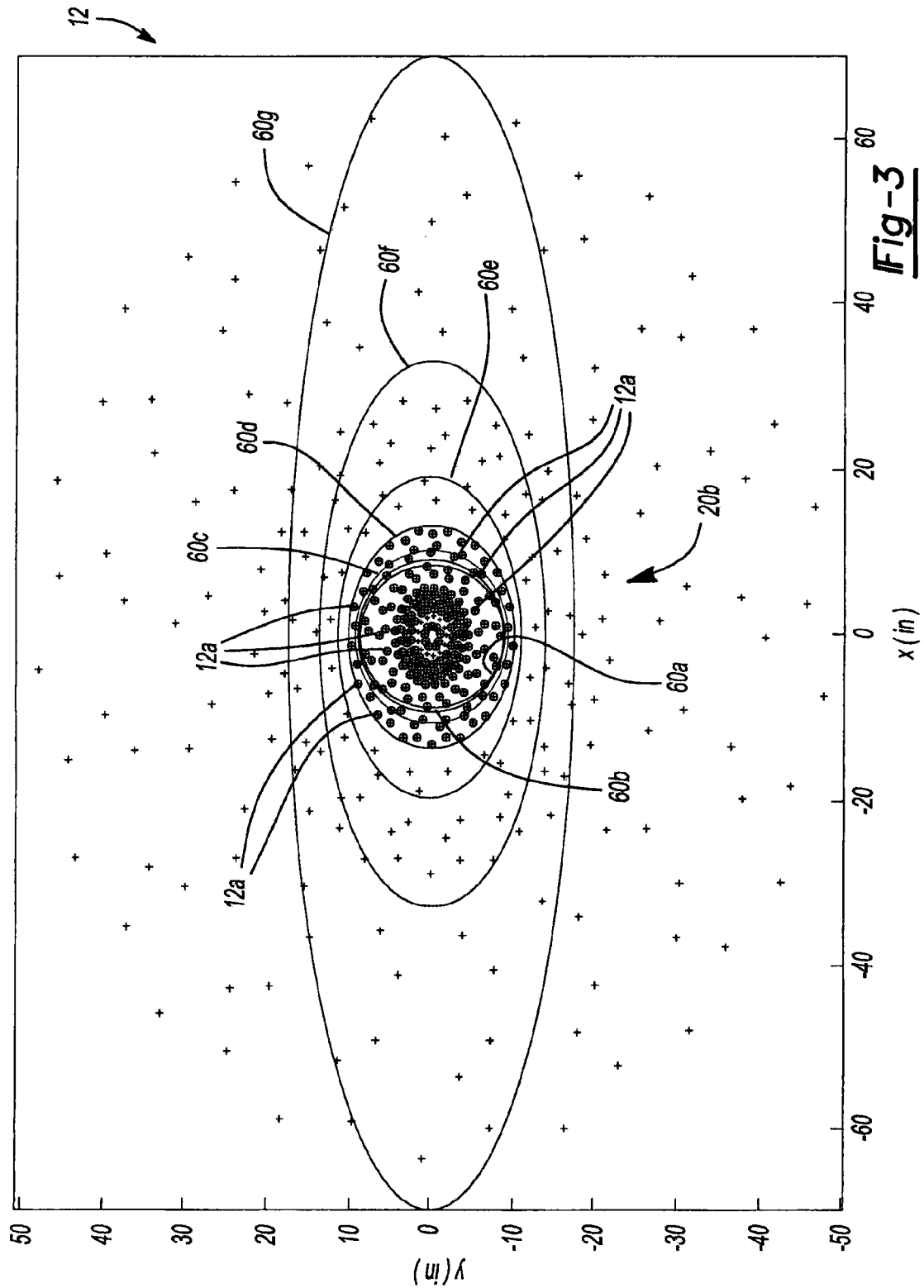

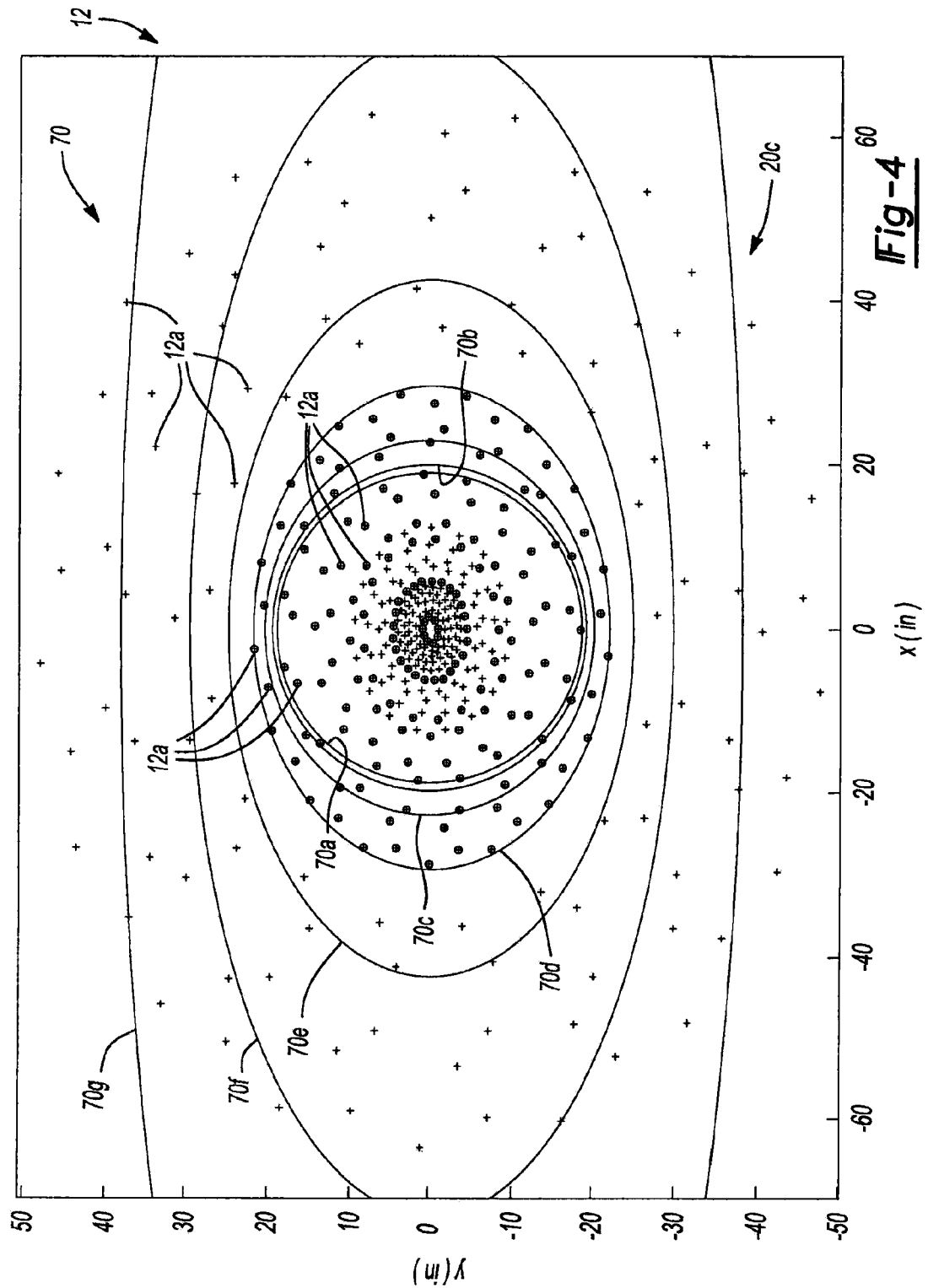

SYSTEM AND METHOD FOR ADAPTABLE APERTURE PLANAR PHASED ARRAY

FIELD

The present disclosure relates generally to planar phased arrays used in noise source location or noise source imaging applications, and more particularly to a system and a method for an adaptable aperture planar phased array for noise source imaging applications at a variety of off-axis or look angles.

BACKGROUND

The statements in this section merely provide background information related to the present disclosure and may not constitute prior art.

Phased arrays, and particularly aeroacoustic phased arrays, have become a standard measurement tool for noise engineering. Such phased arrays are frequently used in development tests of various products such as aircraft, and employed in wind tunnels to enable simultaneous aerodynamic and acoustic data acquisition.

The present disclosure is directed to the problem of designing a planar phased array which is useful across a broad range of frequencies, and where the available number of sensors (i.e. microphones) in the array is restricted such that a regular (i.e., equally spaced element) array cannot be achieved with intra-sensor spacing meeting the half-wavelength criteria typically required to avoid spatial aliasing contamination in source maps or projected beams. A particular problem for such planar arrays is where the primary direction for beamforming is substantially off-axis of the array. This is an especially common problem, for example, for aeroacoustic phased array measurements taken in wind tunnels and flyover noise measurements.

In one example, when the phased array is used within a wind tunnel it is commonly placed along a sideline or wall of the wind tunnel or flat on the ground so that the array orientation is restricted. In such an application, the primary "look" direction will be determined by the position of the model under test with respect to the array position along the wall of the wind tunnel. Beamforming must then be performed off-axis, which reduces the effective aperture of the array. In particular, circular arrays are less effective in beamforming in the off-axis direction and suffer a loss of resolution in the dimension corresponding to the look direction relative to the resolution in the direction perpendicular to the look direction.

In one example, the array may be placed in a stationary position, and the device under test may move relative to the array. In these instances, the off-axis or look angle of the array is defined by where it is desired for the array to look relative to the moving source instead of where the array is moved relative to a stationary source.

It may therefore be desirable to provide a planar array that is particularly well adapted to be used in aeroacoustic applications where off-axis beamforming is required. More specifically, it is a principal object of the present invention to provide a planar array which is especially well suited to performing off-axis beamforming without suffering reduced resolution in the look direction typically experienced with circular arrays in such applications.

SUMMARY

A system for an adaptable aperture planar array for maintaining source resolution as the array moves relative to a source or as the source moves relative to the array is provided. The system includes a first nested array that defines a first aperture responsive to a first range of frequencies. The first aperture is sized based on a desired resolution for the first range of frequencies and an angle between the array and the source. The first aperture includes a first subset of sensor elements. The system also includes a second nested array that defines a second aperture responsive to a second range of frequencies that is less than the first range of frequencies. The second aperture is sized based on a desired resolution for the second range of frequencies and the angle between the array and the source. The second aperture includes a second subset of sensor elements. The first aperture and the second aperture change in size as the array moves in a first direction parallel to a longitudinal axis of the source, which results in a change in the plurality of sensor elements within the first subset and the second subset so that the source resolution for the array remains substantially the same as the angle changes.

In one implementation, a method of maintaining source resolution for an adaptable aperture planar array movable relative to a source is provided. The method includes providing a plurality of sensor elements that each include a coordinate location in the array, and determining a position of the array relative to the source. The method includes computing a first nested array responsive to a first range of frequencies based on the position of the array. The first nested array includes a first subset of the plurality of sensor elements. The method also includes computing a second nested array that is larger than the first nested array. The second nested array includes a second subset of the plurality of sensor elements, which may include at least one sensor element associated with the first subset. The method includes acquiring data associated with the first range of frequencies with the first subset of the plurality of sensor elements, and simultaneously acquiring data associated with the second range of frequencies with the second subset of the plurality of sensor elements. The method also includes determining that the position of the array relative to the source has changed, and recomputing the first nested array based on the changed position of the array. The method also includes recomputing the second nested array based on the changed position of the array, with the recomputing of the first nested array and the second nested array maintaining the source resolution for the array.

A system for an adaptable aperture planar array for maintaining source resolution as the array moves relative to a source is provided. The system includes a source having a longitudinal axis and a plurality of sensor elements each having a coordinate location within the array. The system includes a first nested array defining a first aperture responsive to a first range of frequencies. The first aperture is sized based on an angle between the array and the source, and includes a first subset of the plurality of sensor elements, with each of the plurality of sensor elements within the first subset having coordinate locations within the first aperture. The system includes a second nested array defining a second aperture responsive to a second range of frequencies that is less than the first range of frequencies. The second aperture is larger than the first aperture, and includes a second subset of the plurality of sensor elements. The second subset of the plurality of sensor elements may include at least one of the plurality of sensor elements associated with the first nested array, and each of the plurality of sensor elements within the second subset have coordinate locations within the second aperture. The system also includes a third nested array defining a third aperture responsive to a third range of frequencies that is less than the first range of frequencies and the second range of frequencies. The third aperture is larger than the first aperture and the second aperture, and includes a third subset of the plurality of sensor elements. The third subset of the plurality of sensor elements may include at least one of the plurality of sensor elements associated with the first subset and at least one of the plurality of sensor elements associated with the second subset, and each of the plurality of sensor elements within the third subset have coordinate locations within the third aperture. The system also includes a control module that resizes the first aperture, the second aperture and the third aperture based on the position of the array relative to the source, and changes the plurality of sensor elements associated with the first subset, the second subset and the third subset based on the coordinate locations of the plurality of sensor elements within the resized first aperture, second aperture and third aperture to maintain the source resolution of the array.

Further areas of applicability will become apparent from the description provided herein. It should be understood that the description and specific examples are intended for purposes of illustration only and are not intended to limit the scope of the present disclosure.

BRIEF DESCRIPTION OF THE DRAWINGS

The present disclosure will become more fully understood from the detailed description and the accompanying drawings, wherein:

FIG. 2C is a graph of a third exemplary nested array for the array of FIG. 1 having a look angle defined based on a given design criteria;

FIG. 2D is a graph of a fourth exemplary nested array for the array of FIG. 1 having a look angle defined based on a given design criteria;

FIG. 3 is a graph of a second exemplary set of nested arrays for the array of FIG. 1 at various look angles;

FIG. 4 is a graph of a third exemplary set of nested arrays for the array of FIG. 1 at various look angles;

DETAILED DESCRIPTION

The following description is merely exemplary in nature and is not intended to limit the present disclosure, application, or uses. Although the following description is related generally to a system and method for a highly flexible planar array for source imaging of a mobile platform, it will be understood that the system and method for the sideline array, as described and claimed herein, may be used with any appropriate application where it would be desirable to acquire data regarding propagating energy for a broad range of frequencies at a variety of off-axis or look angles between the array and the source. Therefore, it will be understood that the following discussion is not intended to limit the scope of the appended claims to only mobile platform based systems or acoustic data acquisition. Further, as used herein, the term "module" refers to an application specific integrated circuit (ASIC), an electronic circuit, a processor (shared, dedicated, or group) and memory that executes one or more software or firmware programs, to a combinational logic circuit, and/or to other suitable components that provide the described functionality.

Figure 1:
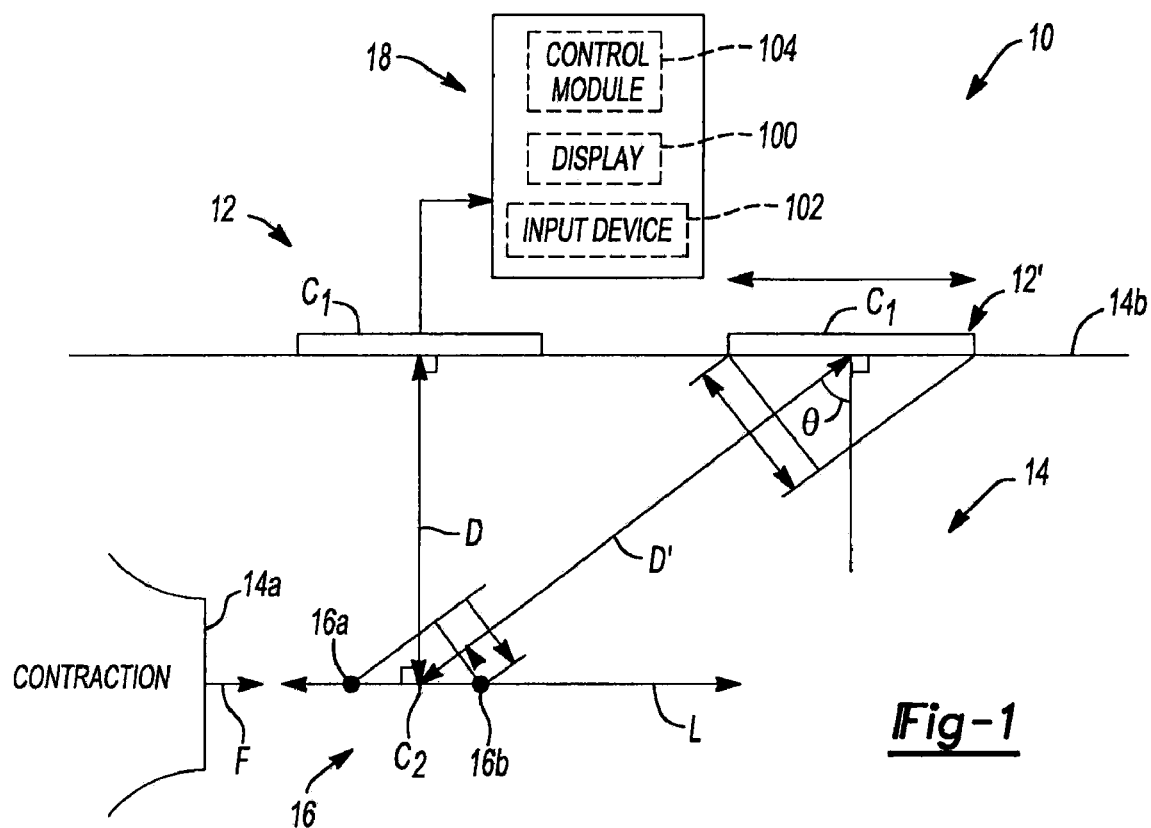
FIG. 1 is a schematic environmental illustration of an adaptable aperture planar phased array according to the principles of the present disclosure for use with an exemplary source, such as a mobile platform.

With reference to FIG. 1, a schematic illustrates an exemplary system 10 that employs an adaptable aperture planar array 12 for source imaging. The system 10 includes a testing area 14, a device under test 16, the array 12 and a workstation 18. The testing area 14 comprises any suitable noise testing facility, such as a closed wind tunnel test facility, an open wind tunnel test facility, a fly-over test facility, etc. In some cases, the testing area 14 may include a wind generation system 14a, which may include a contraction to provide a flow of air through the test facility. In one example, as illustrated, the testing area 14 comprises an open jet wind tunnel test facility, which may contain acoustically treated walls and one or more sidelines 14b that define the testing area 14. As will be discussed, at least one array 12 may be positioned along one of the sidelines 14b, and the device under test 16 may be positioned within the testing area 14 defined by the one or more sidelines 14b.

The device under test 16 may comprise any object desired to undergo noise emission testing, such as a mobile platform, for example, an aircraft, spacecraft, automobile, hovercraft, etc. It will be understood, however, that any suitable object could be tested within the testing area 14, and thus, the system and method described herein may not be limited to only mobile platform test applications. For example, the device under test could comprise a wind turbine. In one example, the device under test 16 has a longitudinal axis L that may be aligned with and substantially parallel to airflow F from the wind generation system 14a, such that the air from the wind generation system 14a impinges directly on the device under test 16. The device under test 16 may include two source locations 16a, 16b. The source location 16a may be positioned at an upstream location on the device under test 16 relative to the wind generation system 14a and the source location 16b may be positioned at a downstream location on the device under test 16.

With continuing reference to FIG. 1, the array 12 is movable along the sideline 14b. With additional reference to FIG. 2, the array 12 is composed of one or more elements 12a, such as microphones, that are capable of acquiring a noise reading. In one example, the array 12 comprises a 416-channel array of microphones, as illustrated in FIG. 3. Generally, each of the elements 12a have an x-coordinate and a y-coordinate location in the array 12, which may be used to select a subset of the data acquired from the array 12, as will be discussed herein. The array 12 is configured to allow for adjustable source resolution when the array 12 is traversed along the respective sideline 14b.

In this regard, with reference to FIG. 1, when the array 12 is traversed along the sideline 14b, three parameters change that impact source resolution at the source locations 16a, 16b. For example, with reference to a center point $C_2$ of the device under test 16, a distance D between the array 12 and the device under test 16 changes from the distance D to a new distance D'. When the array 12 is directly to a side of the device under test 16, the array 12 is said to be at a 90 degree angle to the device under test 16. When the array 12 is traversed along the sideline 14b either upstream (angles <90 degrees) or downstream (angles >90 degrees), the distance D between the array 12 and the device under test 16 increases by a factor $1/\cos(\theta)$ where $\theta$ is a look angle, off-axis angle or the angle between a line connecting a center point $C_2$ of the device under test 16 with a center point $C_1$ of the array 12 and a line normal to the array 12.

Second, the "effective" aperture of the array 12 changes as the array 12 moves relative to the device under test 16. The effective aperture of the array 12 may become smaller as the array 12 is traversed away from 90 degrees. Generally, the effective array aperture is reduced by a factor $\cos(\theta)$, where $\theta$ is the look angle or off-axis angle. Third, sources of noise generated at the source locations 16a and 16b may appear closer together from the point of view of the array 12 as the array 12 is traversed away from 90 degrees. Thus, the ability of the array 12 to resolve these noise sources or separate the sources may be affected. The source separation ability of the array 12 may be reduced by a factor of $\cos(\theta)$ when the source locations 16a and 16b are located on a plane parallel to a plane associated with the array 12, where $\theta$ is the look angle or off-axis angle.

The reduction in source resolution of the array 12 as the array 12 is traversed along the sideline 14b from 90 degrees may be represented as $\cos^3(\theta)$ in the direction of the movement of the array 12 (x-coordinate component). In a direction perpendicular to the movement of the array 12 (y-coordinate component), the reduction in resolution may be represented as $\cos(\theta)$. In order to maintain the resolution of the array 12, the array 12 of the present disclosure includes one or more sets of nested arrays 20 formed of the array elements 12a.

Figure 5:
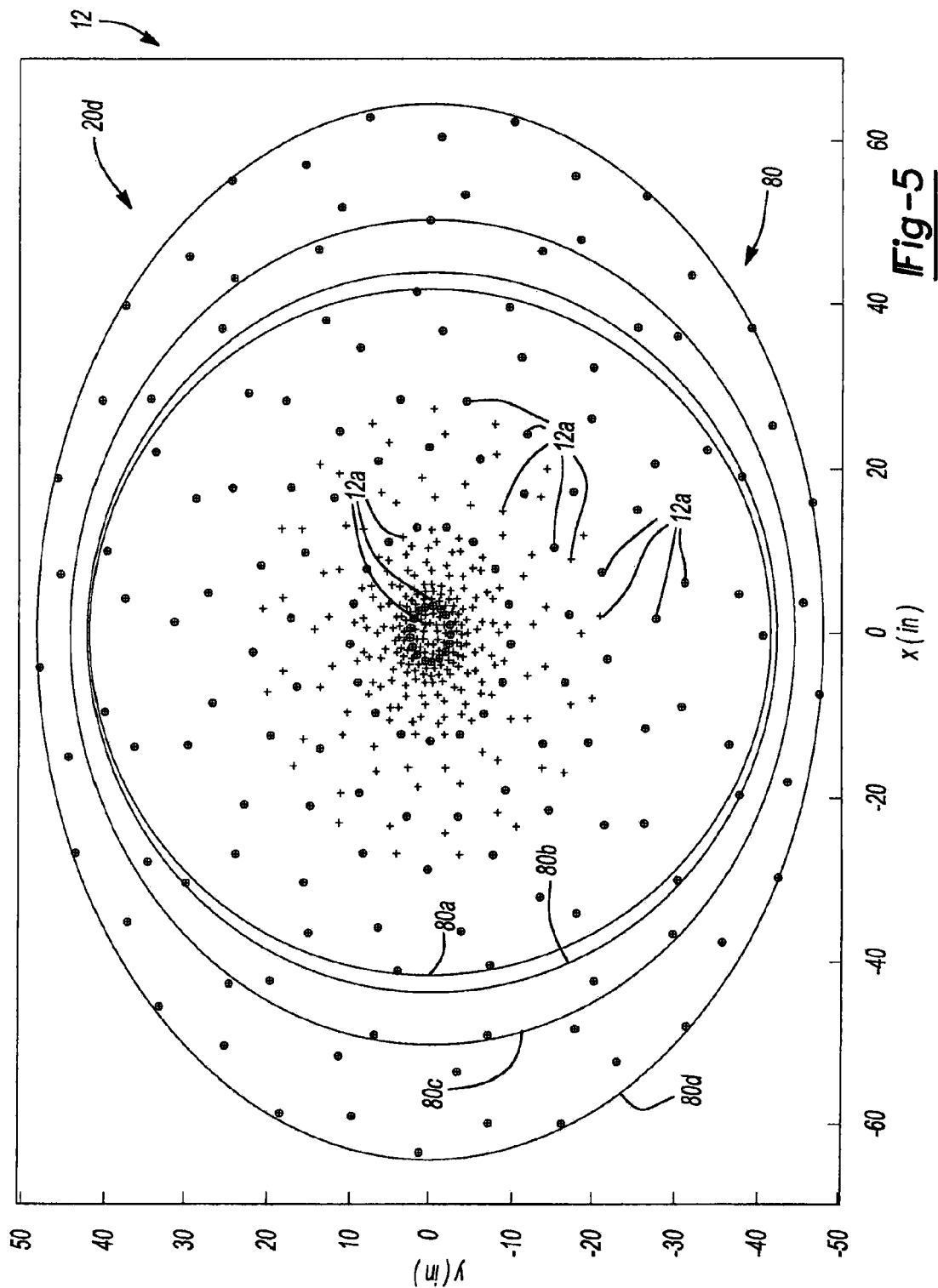
FIG. 5 is a graph of a fourth exemplary set of nested arrays for the array of FIG. 1 at various look angles.

For example, with reference to FIGS. 2-5, the array 12 may include a first set of nested arrays 20a (FIG. 2), a second set of nested arrays 20b (FIG. 3), a third set of nested arrays 20c (FIG. 4) and a fourth set of nested arrays 20d (FIG. 5). The array elements 12a may be associated with each of the nested arrays 20 based upon their coordinate location in the array 12.

In this regard, once the first set of nested arrays 20a is defined, the array elements 12a present within a boundary defined by the first set of nested arrays 20a may be associated with the first set of nested arrays 20a. Thus, selected elements 12a present in the boundary defined by the second set of nested arrays 20b become associated with the second set of nested arrays 20b, selected elements 12a present within the boundary defined by the third set of nested arrays 20c are associated with the third set of nested arrays 20c, and selected elements 12a present within the boundary defined by the fourth set of nested arrays 20d are associated with the fourth set of nested arrays 20d. As will be discussed, in certain instances, the elements 12a may be associated with one or more nested arrays 20, which enables the array 12 to provide accurate measurements and maintain source resolution over a range of frequencies without requiring additional arrays 12. It should be understood, that although four sets of nested arrays 20 are described and illustrated herein, any number of sets of nested arrays 20 with any number of arrays per set could be formed and utilized in the array 12 based on the needs of the application, availability of elements 12a, limitations on overall size, etc.

The sets of nested arrays 20 are created by first defining nested arrays for a single look angle $\theta$ and then using an array aperture resizing method to define nested arrays for other look angles $\theta$. For example, nested arrays within the array apertures 50d, 60d, 70d, and 80d are designed for the look angle $\theta$ of 30 degrees. The other nested arrays within the array apertures 50a-c, 50e-g, 60a-c, 60e-g, 70a-c, 70e-g, and 80a-c are then defined using an array aperture resizing method as will be described herein.

As the system and method used to generate the nested arrays within the array apertures 50d, 60d, 70d, and 80d are described in commonly assigned U.S. Pat. No. 6,583,768, incorporated herein by reference, they will not be discussed in great detail herein. Briefly, however, in order to generate the first nested array within the array aperture 50d, a non-redundant array is designed to have a shape that corresponds with the desired source mapping characteristic. For example, with reference to FIG. 2A, the first nested array within the array aperture 50d may be configured to acquire the highest frequencies of interest, and thus, may have a relatively small aperture 50d to provide the desired source resolution for the range of frequencies in which the first nested array within the array aperture 50d may be employed. In one example, the nested arrays within the array apertures 50d, 60d, 70d, and 80d comprise a point design nested array in which the look angle or off-axis angle $\theta$ is 30 degrees.

Figure 2:
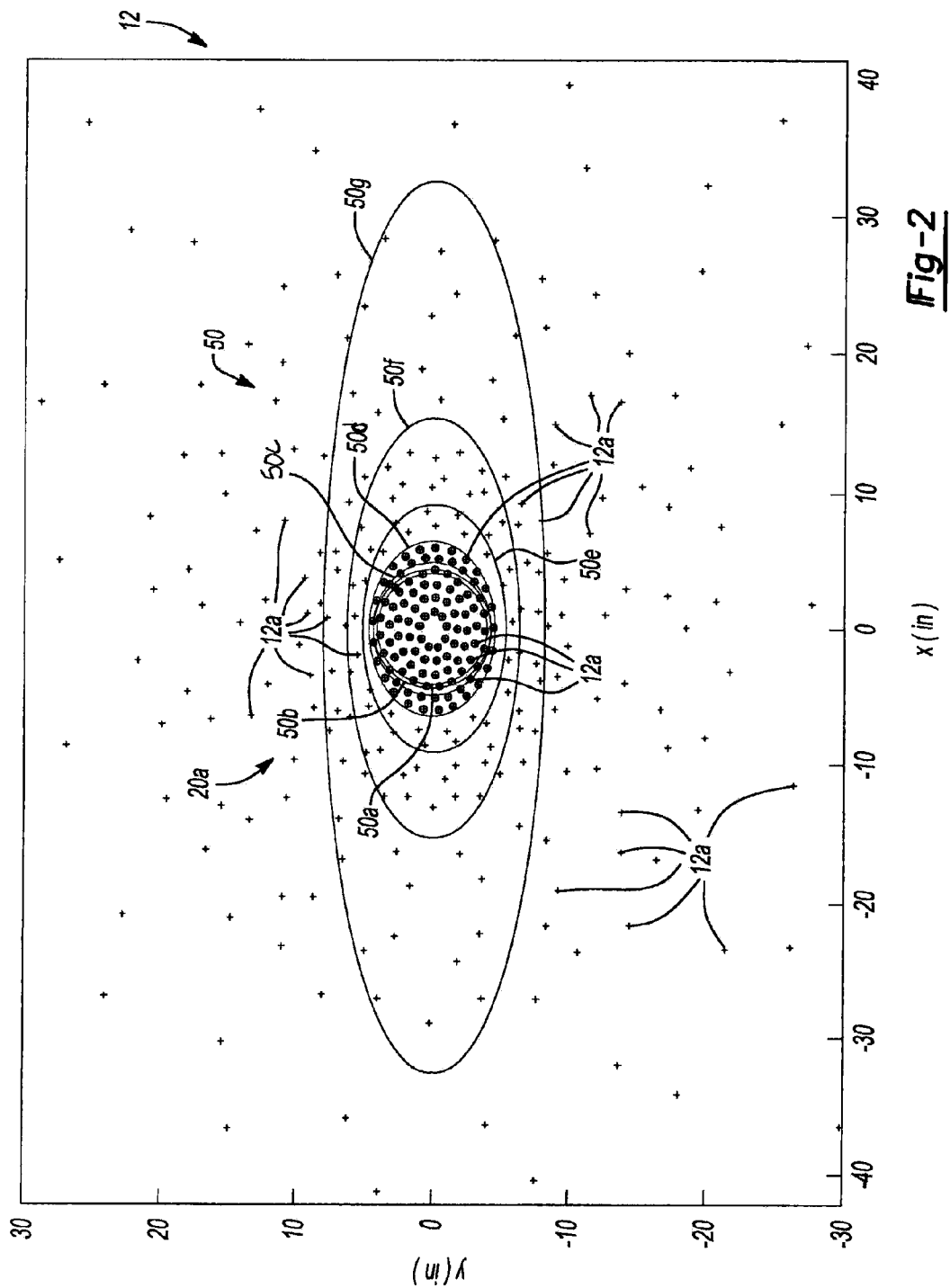
FIG. 2 is a graph of a first exemplary set of nested arrays for the array of FIG. 1 at various look angles.
Figure 2A:
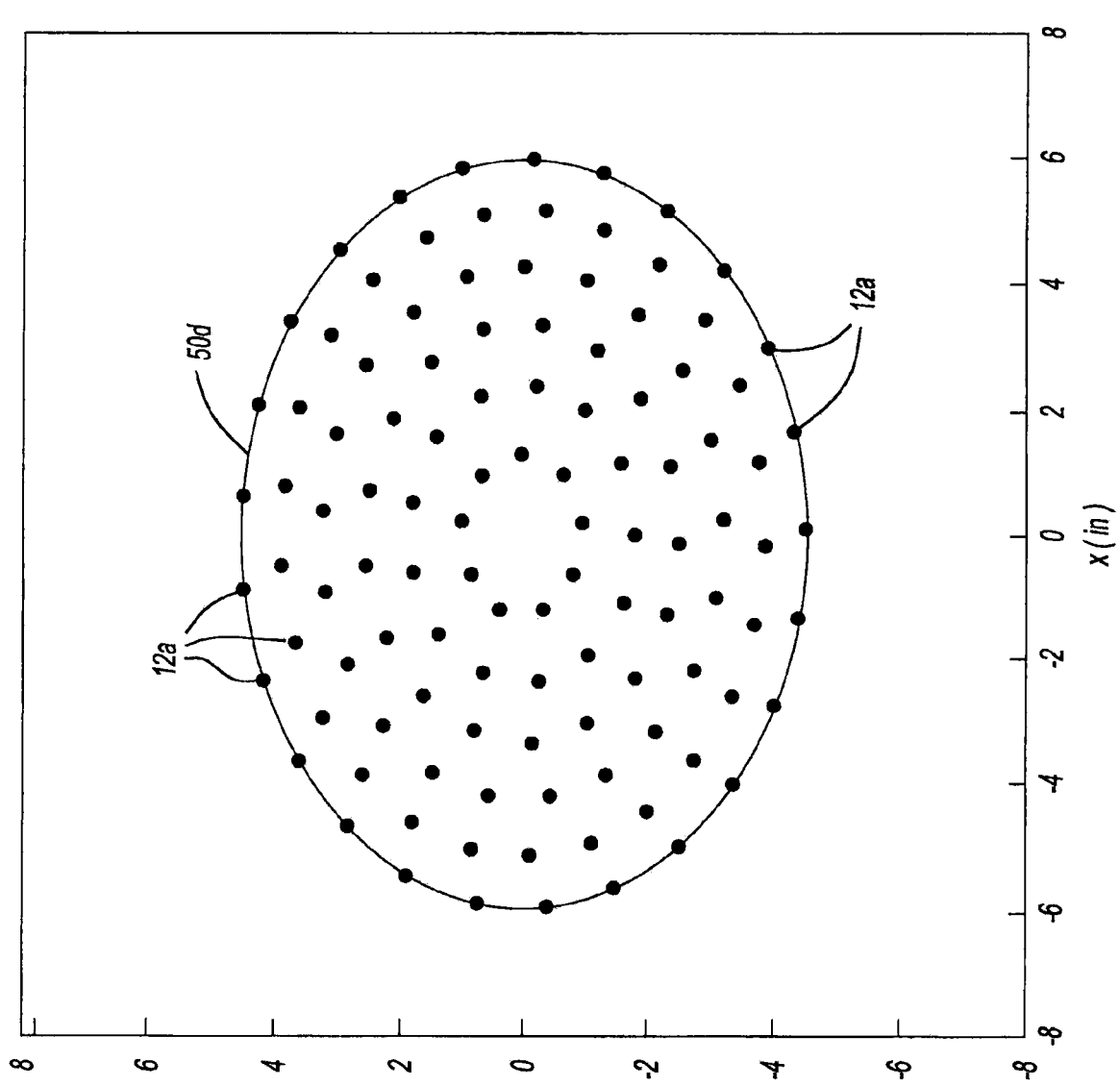
FIG. 2A is a graph of a first exemplary nested array of FIG. 2 having a look angle defined based on a given design criteria.

In this regard, with reference to FIG. 2A, the first nested array within the array aperture 50d may be designed for a particular design point, such as, a look angle $\theta$ of 30 degrees. In order to form the first nested array within the array aperture 50d, a non-redundant circular array may be formed, and the x coordinates of the elements 12a associated with this array may then be divided by $\cos^2\theta$ to stretch the circular array for the 30 degree look angle $\theta$ to produce the array within the array aperture 50d.

Figure 2B:
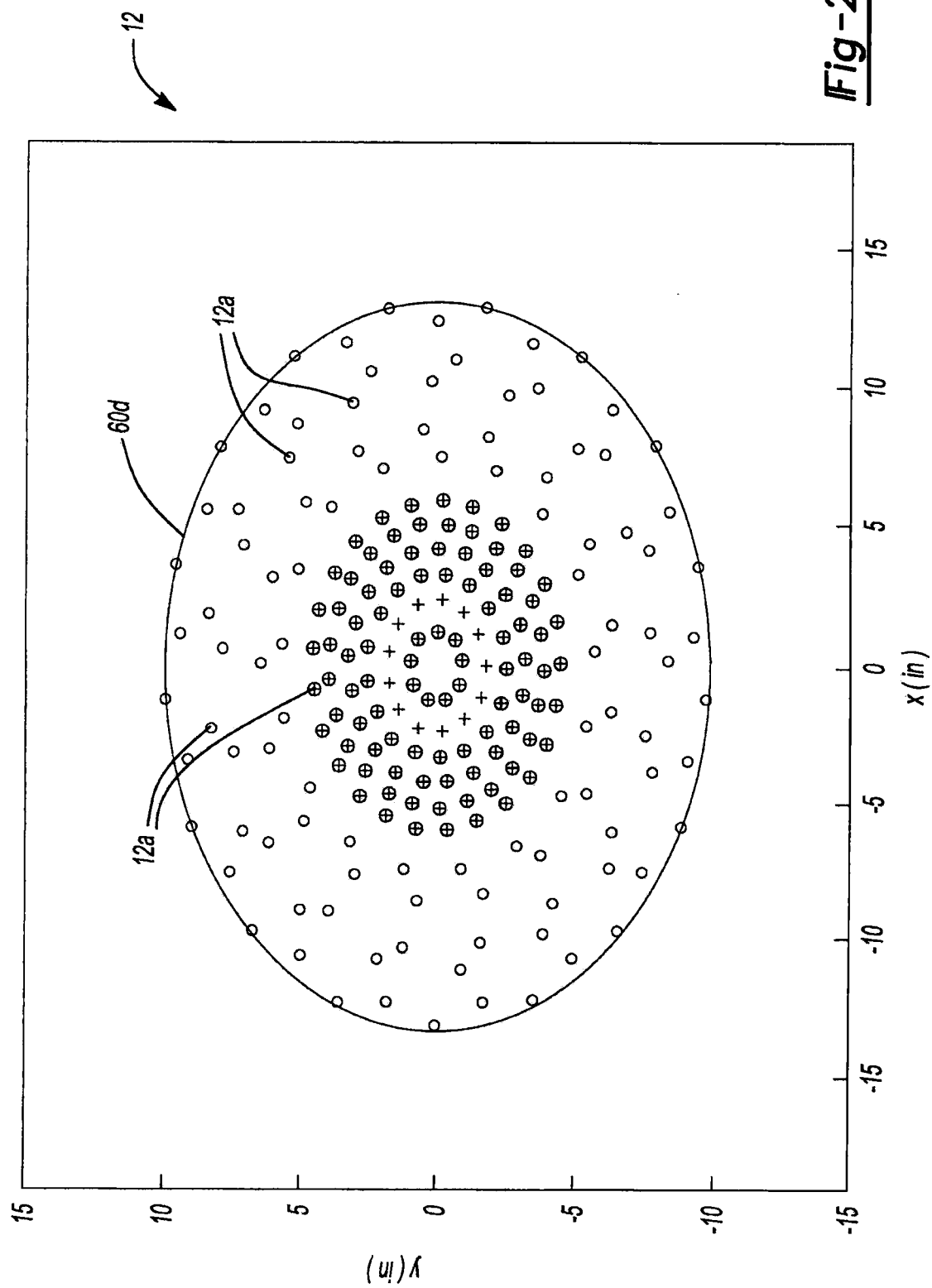
FIG. 2B is a graph of a second exemplary nested array for the array of FIG. 1 having a look angle defined based on a given design criteria.

Then, with reference to FIG. 2B, the second nested array within the array aperture 60d may be designed for the look angle $\theta$ of 30 degrees. Generally, the second nested array within the array aperture 60d may be configured to acquire a range of frequencies below that for which the first nested array within the array aperture 50d is designed, such as for a range of mid-to-high frequencies. As noise at lower frequencies may be less directive than noise at higher frequencies, the second nested array within the array aperture 60d may have a larger aperture size than the first nested array aperture 50d.

In this regard, as the frequency decreases, the size of the aperture of the array increases to maintain the same resolution. Typically, the second nested array within the array aperture 60d is designed using the same process as the first nested array within the array aperture 50d, and may include the elements 12a shown. The second nested array within the array aperture 60d may reuse some of the elements 12a associated with the first nested array within the array aperture 50d. Generally, an aperture of the second nested array 60d may be about twice as large as an aperture of the first nested array 50d, but it should be understood that the ratio of the aperture sizes between the second nested array 60d and the first nested array 50d could be any number greater than 1.

For example, the second nested array within the array aperture 60d may typically have about the same number of elements 12a as the first nested array within the array aperture 50d, in which about half of the elements 12a are in common with those from the first nested array within the array aperture 50d, and about half are new elements 12a within the array 12. In one example, as illustrated in FIG. 2B, (o) may represent new elements 12a that are associated with the second nested array within the array aperture 60d, (⊕) may represent elements 12a that are in common with the first nested array within the array aperture 50d, and (+) may represent elements 12a from the first nested array within the array aperture 50d that are not used in the second nested array within the array aperture 60d. It should be understood, however, that the second nested array within the array aperture 60d could have more or less elements 12a than the first nested array within the array aperture 50d and the ratio of elements 12a in common with the first nested array within the array aperture 50d to new elements 12a may be greater or smaller.

With reference to FIG. 2C, the third nested array within the array aperture 70d may be computed next for the look angle θ of 30 degrees. Generally, the third nested array within the array aperture 70d may be configured to acquire a range of frequencies below that for which the first nested array within the array aperture 50d and second nested array within the array aperture 60d are designed, such as for ranges of mid-to-low frequencies. As noise at lower frequencies may be less directive than noise at high or mid-range frequencies, the third nested array within the array aperture 70d may have a larger aperture size than the first nested array within the array aperture 50d and the second nested array within the array aperture 60d. Generally, an aperture of the third nested array 70d may be about four times as large as the aperture of the first nested array 50d, and the ratio of the apertures between the third nested array 70d and the second nested array 60d may be any number greater than one.

Typically, the third nested array within the array aperture 70d may reuse some of the elements 12a associated with both the first nested array within the array aperture 50d and the second nested array within the array aperture 60d. In one example, the third nested array within the array aperture 70d may typically have about the same number of elements 12a as the second nested array within the array aperture 60d, in which about one-fourth of the elements 12a are in common with those from the first nested array within the array aperture 50d, about one-fourth of the elements 12a are in common with those from the second nested array within the array aperture 60d, and about one-half are new elements 12a within the array 12. In one example, as illustrated in FIG. 2C, (o) may represent new elements 12a that are associated with the third nested array within the array aperture 70d, (⊕) may represent elements 12a that are in common with the first nested array within the array aperture 50d and the second nested array within the array aperture 60d, and (+) may represent elements 12a from the first nested array within the array aperture 50d and second nested array within the array aperture 60d that are not used in the third nested array within the array aperture 70d. It should be understood, however, that the third nested array within the array aperture 70d could have more or less elements 12a than the second nested array within the array aperture 60d and the ratio of elements 12a in common with the first nested array within the array aperture 50d, the second nested array within the array aperture 60d and the new elements 12a may be greater or smaller.

With reference to FIG. 2D, the fourth nested array 80d may be designed for the look angle θ of 30 degrees. Generally, the fourth nested array within the array aperture 80d may be configured to acquire a range of frequencies below that for which the first nested array within the array aperture 50d, the second nested array within the array aperture 60d and the third nested array within the array aperture 70d are designed, such as for a range of low frequencies. As noise at low frequencies may be less directive than noise at high or mid-range frequencies, the fourth nested array within the array aperture 80d may have a larger aperture size than the third nested array within the array aperture 70d. Generally, an aperture of the fourth nested array 80d may be about eight times as large as the first nested array 50d, and the ratio of the apertures between the fourth nested array 80d and the third nested array 70d may be any number greater than one.

Typically, the fourth nested array within the array aperture 80d may reuse some of the elements 12a associated with the first nested array within the array aperture 50d, the second nested array within the array aperture 60d and the third nested array within the array aperture 70d. In one example, the fourth nested array within the array aperture 80d may typically have about the same number of elements 12a as the third nested array within the array aperture 70d, in which about one-sixth of the elements 12a are in common with those from the first nested array within the array aperture 50d, about one-sixth of the elements 12a are in common with those from the second nested array within the array aperture 60d, about one-sixth of the elements 12a are in common with those from the third nested array within the array aperture 70d and about one-half are new elements 12a within the array 12.

In one example, as illustrated in FIG. 2D, (o) may represent new elements 12a that are associated with the fourth nested array within the array aperture 80d, (⊕) may represent elements 12a that are in common with the first nested array within the array aperture 50d, the second nested array within the array aperture 60d and the third nested array within the array aperture 70d, and (+) may represent elements 12a from the first nested array within the array aperture 50d, second nested array within the array aperture 60d and third nested array within the array aperture 70d that are not used in the fourth nested array within the array aperture 80d. It should be understood, however, that the fourth nested array within the array aperture 80d could have more or less elements 12a than the third nested array within the array aperture 70d and the ratio of elements 12a in common with the first nested array within the array aperture 50d, the second nested array within the array aperture 60d, the third nested array within the array aperture 70d and the new elements 12a may be greater or smaller.

With reference back to FIG. 1, in order to compensate for the look angle θ of the array 12 relative to center point $C_2$ of the device under test 16, the x-coordinates of the array elements 12a (microphone positions) may be divided by $\cos^2 \theta$ where θ is the look angle or off-axis angle associated with the position of the array 12 so that when the array 12 is in the position corresponding to the look angle θ, the resolution in the x-direction and y-direction will be the same. In this regard, if the lateral (x-coordinate) dimension of the generated first nested array within the array aperture 50d is parallel to the longitudinal axis L of the device under test 16, the vertical (y-coordinate) dimension of the generated first nested array within the array aperture 50d is perpendicular to the longitudinal axis L of the device under test 16, and the array 12 is moved to a different location such that the look angle is not θ, then the generated first nested array within the array aperture 50d will not give the same resolution in either the y-direction or the x-direction because of the new look angle that is not equal to θ of the first nested array within the array aperture 50d relative to the device under test 16.

In one example, given that the first nested array within the array aperture 50d was generated based on a look angle θ of 30 degrees, in order to generate a first nested array with a look angle θ that is different than 30 degrees such as first nested arrays within the array apertures 50a-c or first nested arrays within the array apertures 50e-g, the array within the array aperture 50d is resized by selectively removing elements 12a from the nested array within the array aperture 50d or adding array elements 12a from nested arrays within the array apertures 60d, 70d, and 80d. In one example the x-coordinates of the array aperture 50d are multiplied by $\cos^3(\theta)$ with the look angle θ equal to 30 degrees to compensate for the off-axis position of the first nested array within the array aperture 50d. Then, the y-coordinates of the array aperture 50d are multiplied by $\cos(\theta)$ with the look angle θ equal to 30 degrees to compensate for the change in distance D between the array 12 and the device under test 16. This generates a 0 degree array aperture 50a, illustrated in FIG. 2. Given the 0 degree array aperture 50a, in order to modify the array to compensate for a look angle θ that is different from zero, the x-coordinates of the 0 degree array aperture 50a may be divided by $\cos^3(\theta)$ and the y-coordinates may be divided by $\cos(\theta)$, in which the look angle θ is equal to the new look angle θ associated with the position of the array 12 relative to the object under test 16.

For example, as illustrated in FIG. 2, the aperture of the first nested array 50d may be modified from the look angle θ of 30 degrees to account for various look angles θ, such as zero degrees (aperture 50a), 10 degrees (aperture 50b), 20 degrees (aperture 50c), 40 degrees (aperture 50e), 50 degrees (aperture 50f), and 60 degrees (aperture 50g). Note that not all of the elements 12a within the first nested array aperture 50d may be utilized at each look angle θ or elements in addition to those within the first nested array aperture 50d may be utilized as selected elements 12a within the respective apertures 50a-50g will be utilized for the corresponding look angle θ.

In this regard, various elements 12a may be associated with the first nested array depending upon the aperture 50. For example, if the array aperture is 0 degrees, then only elements 12a within the boundary defined by the aperture 50a may be associated with the first nested array. As a further example, if the array aperture is 40 degrees, then the elements 12a associated with the first nested array 50e may include the elements 12a from the first nested array within the array aperture 50d and the elements 12a from the second nested array within the array aperture 60d, the third nested array within the array aperture 70d, and the fourth nested array within the array aperture 80d that are between the boundary defined by the aperture 50d and the boundary defined by the aperture 50e. Thus, as the look angle θ associated with the first nested array decreases with respect to the look angle θ of the design point, elements 12a may be pruned or removed from the first nested array within the array aperture 50d, and as the look angle θ associated with the first nested array increases relative to the look angle θ associated with the design point, the elements 12a associated with the respective aperture of the first nested array 50d may grow or be added from the adjacent second nested array within the array aperture 60d, third nested array within the array aperture 70d, and fourth nested array within the array aperture 80d.

In the example of FIG. 2, the elements 12a associated with each respective aperture 50 are illustrated as a circled plus sign (⊕) or a plus sign (+), in which the elements represented by the circled plus sign (⊕) are those elements 12a originally associated with the first nested array within the array aperture 50d (i.e. those elements 12a associated with the first nested array within the array aperture 50d generated with the design point look angle θ of 30 degrees).

With reference to FIG. 3, the second nested arrays within the array apertures 60 may be computed next for the new look angle ⊕ that is different than the design point look angle ⊕ of 30 degrees. As the second nested arrays within the array apertures 60 may be computed in the same manner as the first nested arrays within the array apertures 50 described above, the process for converting the second nested array within the array aperture 60d to a new look angle θ will not be discussed in great detail herein. Briefly, however, the x-coordinates of the aperture associated with the second nested array 60d may be divided by $\cos^3(\theta)$ with the look angle θ equal to 30 degrees to compensate for the off-axis position of the second nested array within the array aperture 60d, and the y-coordinates of the aperture may be multiplied by $\cos(\theta)$ with the look angle θ equal to 30 degrees to compensate for the change in distance D. This generates a 0 degree aperture 60a for the second nested array, illustrated in FIG. 3. Given the 0 degree array aperture 60a, in order to modify the array to compensate for a look angle θ that is different from zero, the x-coordinates associated with the 0 degree array aperture 60a may be divided by $\cos^3(\theta)$ and the y-coordinates may be divided by $\cos(\theta)$, in which the look angle θ is equal to the new look angle θ associated with the position of the array 12 relative to the object under test 16.

In one example, as illustrated in FIG. 3, the aperture 60d of the second nested array may be modified from the look angle θ of 30 degrees like the first nested array aperture 50d to account for various look angles θ, such as zero degrees (aperture 60a), 10 degrees (aperture 60b), 20 degrees (aperture 60c), 40 degrees (aperture 60e), 50 degrees (aperture 60f), and 60 degrees (aperture 60g), as will be discussed herein. Note that not all of the elements 12a within the second nested array aperture 60a, 60b, 60c, 60e, 60f, or 60g will be utilized at each look angle θ, but rather, only selected non-redundant elements 12a that fall within the respective aperture 60a-60g may be employed with the second nested array. In this regard, as the look angle θ associated with the second nested array decreases with respect to the look angle θ of the design point, elements 12a may be pruned or removed from the second nested array within the array aperture 60d. Similarly, as the look angle θ associated with the second nested array increases relative to the look angle θ associated with the design point, the elements 12a associated with the respective aperture of the second nested array 60d may grow or be added from the third nested array within the array aperture 70d and fourth nested array within the array aperture 80d.

With reference to FIG. 4, the third nested arrays within the array apertures 70 may be computed for the new look angle θ that is different than the design point look angle θ of 30 degrees in the same manner employed for both the first nested arrays within the array apertures 50 and the second nested arrays within the array apertures 60.

In one example, as illustrated in FIG. 4, the aperture of the third nested array 70d may be modified from the look angle θ of 30 degrees to similarly account for various look angles θ, such as zero degrees (aperture 70a), 10 degrees (aperture 70b), 20 degrees (aperture 70c), 40 degrees (aperture 70e), 50 degrees (aperture 70f), and 60 degrees (aperture 70g), as discussed herein. Note that not all of the elements 12a associated with the array 12 will be utilized at each look angle θ. Rather, as discussed with regard to the first nested arrays within the array apertures 50 and the second nested arrays within the array apertures 60, only selected non-redundant elements 12a that fall within the respective apertures 70a-70g may be employed with the third nested arrays within the array apertures 70.

With reference to FIG. 5, the fourth nested array 80 may be generated in the same manner employed for the first nested array 50, the second nested array 60 and the third nested array 70. As illustrated in FIG. 5, the aperture of the fourth nested array 80d may be modified from a look angle θ of 30 degrees similar to the first nested array aperture 50d to account for various look angles θ, such as zero degrees (aperture 80a), 10 degrees (aperture 80b), and 20 degrees (aperture 80c), as discussed herein. Note that not all of the elements 12a within the array 12 will be utilized at each look angle θ. Rather, as discussed, only selected non-redundant elements 12a that fall within the respective aperture 80a-80d may be employed within the fourth nested arrays within the array apertures 80.

It should be noted that all of the elements 12a associated with the sets of nested arrays 20 may be non-redundant such that any combination (subset) of the elements 12a will produce a non-redundant nested array. The use of non-redundant elements 12a enables the apertures 50, 60, 70, 80 of the sets of nested arrays 20a-20d to be expanded or contracted to account for variation in look angles or off-axis angles θ, as illustrated in FIGS. 2-5, without substantially affecting the broadband source mapping of the resultant nested arrays 20. Thus, these resized arrays 20 may be used to selectively process acquired data regarding the device under test 16 from the new position or look angle θ while maintaining the source resolution associated with the prior position of the array 12 relative to the device under test 16.

With reference to FIG. 1, the workstation 18 includes a display 100, a user input device 102 and a control module 104. The workstation 18 may also include or be connected to a data processor, and memory to hold instruction and data. The workstation 18 may provide facilities for displaying data acquired by the array 12, saving, digitally manipulating, or printing a hard copy of the data received from the array 12. The user input device 102 may comprise any device that may enable a user to interface with the workstation 18, such as a touchpad, touch pen, touch screen, keyboard, mouse, wireless mouse, or a combination thereof. The user input device 102 allows a user to provide inputs to adjust the display settings of the display 100, and adjust the look angle θ of the array 12, as further discussed herein.

Figure 6:
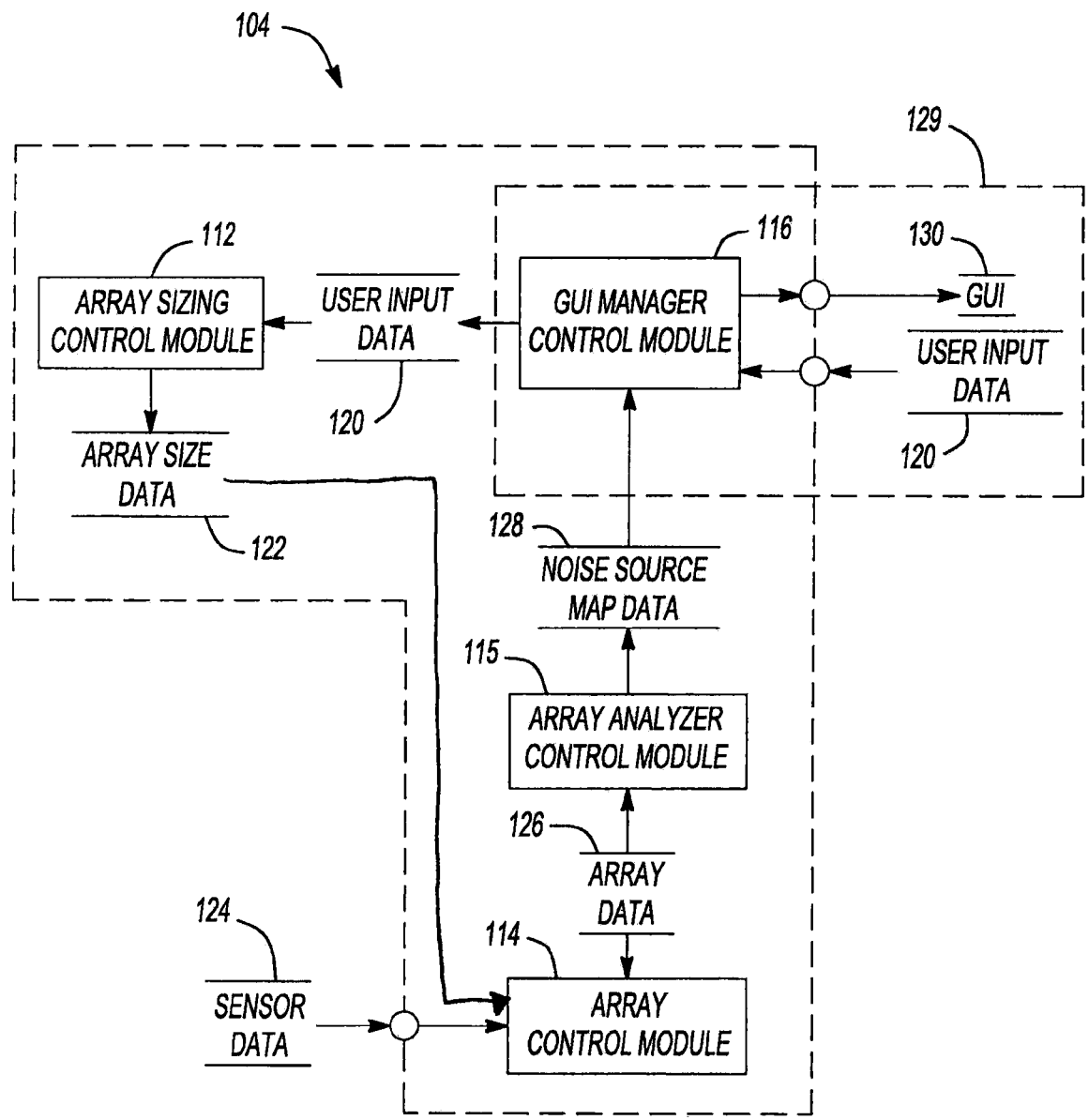
FIG. 6 is a dataflow diagram illustrating a control system for use with the array of FIG. 1.

The control module 104 determines the aperture sizes for the sets of nested arrays 20 depending upon the look angles θ received from the user input device 102. With reference to FIG. 6, a dataflow diagram illustrates various components of a control system that is embedded within the control module 104. Various embodiments of the control module 104 may include any number of sub-modules embedded within the control module 104. The sub-modules shown in FIG. 6 may be combined and/or further partitioned to similarly control the size of the apertures 50, 60, 70, 80 of the sets of nested arrays 20. Inputs to the control module 104 are received from other control modules associated with the array 12, and/or determined by other sub-modules within the control module 104. In FIG. 6, the control module 104 includes an array sizing control module 112, an array control module 114, an array analyzer control module 115 and a graphical user interface (GUI) manager control module 116.

The array sizing control module 112 receives as input user input data 120. The user input data 120 comprises the look angle θ that represents the position of the array 12 relative to the source 16. Based on the look angle θ, the array sizing control module 112 sets array size data 122 for the array control module 114. The array size data 122 comprises the aperture 50, 60, 70, 80 for each of the nested arrays within the array 12 for the given look angle θ.

The array control module 114 receives as input the array size data 122 and sensor data 124. The sensor data 124 comprises readings from each of the elements 12a of the array 12. Given the array size data 122, the array control module 114 determines the elements 12a present within the nested arrays 20, and sets array data 126 for the array analyzer control module 115. The array data 126 comprises the sensor data 124 associated with the nested arrays 20, based on the array size data 122. The array analyzer control module 115 receives as input the array data 126. Based on the array data 126, the array analyzer control module 115 sets noise source map data 128 for the for the GUI manager control module 116. The noise source map data 128 includes noise maps that illustrate the source regions associated with the device under test 16.

The GUI manager control module 116 receives as input the user input data 120 and the noise source map data 128. The GUI manager control module 116 sets the user input data 120 for the array sizing control module 112. The GUI manager control module 116 outputs a GUI 130. The GUI manager control module 116, the user input data 120 and the GUI 130 may collectively be viewed as forming a graphical user interface subsystem of the control module 104. The GUI 130 provides a user with noise maps from the noise source map data 128 that illustrates the noise sensed by the array elements 12a associated with the nested arrays 20 for a given look angle θ, with the look angle θ provided by the user input data 120. It should be understood that the GUI 130 is an exemplary output form for the noise source map data 128, and that any suitable means could be employed to provide the user with the noise source map data 128, such as a data file, etc.

Figure 7:
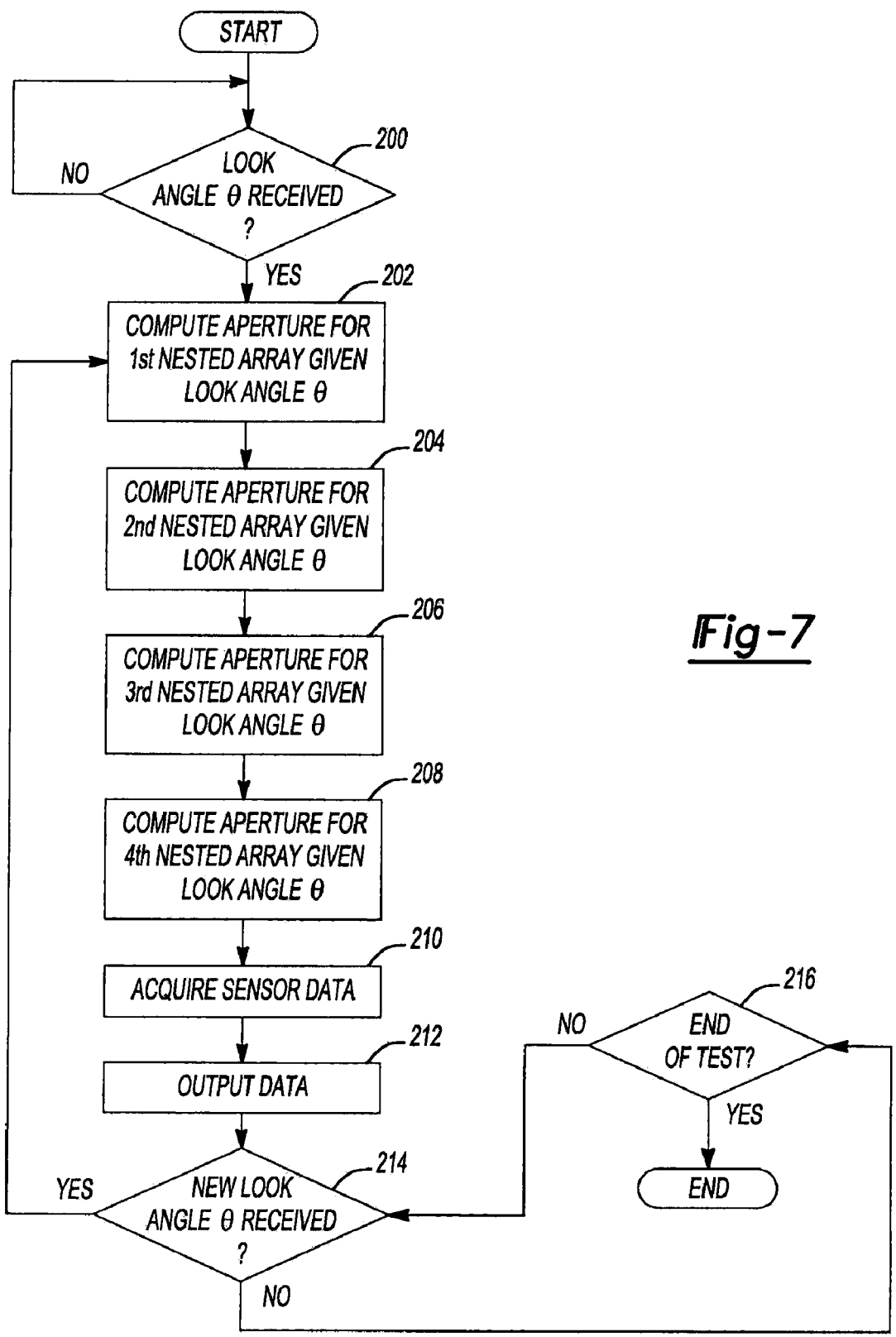
FIG. 7 is a process flow diagram illustrating an operational sequence for the control system of FIG. 6.

With additional reference to FIG. 7, a process flow diagram illustrates a sequence performed by the control module 104. In operation 200, the control module 104 determines if a look angle θ for the array 12 has been received from the user input device 102. If a look angle θ has been received, then the method goes to operation 202. Otherwise, the method loops to operation 200.

At operation 202, the method computes the aperture 50 for the first nested array given the look angle θ. Then, at operation 204, the method computes the aperture 60 for the second nested array given the look angle θ. At operation 206, the method computes the aperture 70 for the third nested array given the look angle θ, and at operation 208, the method computes the aperture 80 for the fourth nested array based on the look angle θ. Note that although not illustrated herein, a similar operation may be repeated as necessary to account for additional nested arrays within the array 12.

At operation 210, the method acquires the sensor data 124 from each of the elements 12a within the array 12. Then, at operation 212, the method outputs the noise source map data 128 as the GUI 130, which provides the user with the results from processing the sensor data 124 associated with the elements 12a within each of the nested arrays 20.

At operation 214, the method determines if the user has input a new look angle θ for the array 12 relative to the source 16. If a new look angle θ has been input at operation 214, then the method loops to operation 202. If the user has not input a new look angle θ, then the method determines at operation 216 if it is the end of the noise test for the device under test 16. If it is the end of the test, then the method ends. Otherwise, the method loops to operation 214.

While specific examples have been described in the specification and illustrated in the drawings, it will be understood by those of ordinary skill in the art that various changes may be made and equivalents may be substituted for elements thereof without departing from the scope of the present disclosure as defined in the claims. Furthermore, the mixing and matching of features, elements and/or functions between various examples is expressly contemplated herein so that one of ordinary skill in the art would appreciate from this disclosure that features, elements and/or functions of one example may be incorporated into another example as appropriate, unless described otherwise, above. Moreover, many modifications may be made to adapt a particular situation or material to the teachings of the present disclosure without departing from the essential scope thereof. Therefore, it is intended that the present disclosure not be limited to the particular examples illustrated by the drawings and described in the specification as the best mode presently contemplated for carrying out this disclosure, but that the scope of the present disclosure will include any embodiments falling within the foregoing description and the appended claims.

For example, while the array 12 has been described as being resizable to account for movement of the array 12 in a direction generally parallel to the longitudinal axis of the device under test 16, those of skill in the art will appreciate that the present disclosure, in its broadest aspects, may be constructed somewhat differently. In this regard, the array 12 may also be resized to account for the array 12 being moved in a direction perpendicular to the longitudinal axis of the device under test 16. In this example, starting from the 0 degree aperture array, each x-coordinate location may be divided by $\cos(\theta)$ and each y-coordinate location may be divided by $\cos^3(\theta)$ to account for the new look angle $\theta$ resulting from the movement of the array 12 in a direction perpendicular to the longitudinal axis of the device under test 16. In an alternative example, the array 12 could be in a fixed position relative to a moving device under test 16. In this alternative example, the array 12 may be sampled by the control module 104 such that the data obtained from the elements 12a accounts for the array 12 looking at the source under test 16 from a variety of look angles $\theta$. In other words, an array 12 may be defined for any number of desired locations of the moving device under test 16, with the look angle $\theta$ based on where the array 12 is looking rather than where the array 12 is positioned relative to a reference point. In yet another example, the array 12 may be in a fixed position and the device under test 16 may be in a fixed position. The device under test 16 may have an extended source region such that when the array 12 is "looking" at various points in the extended source region the look angle varies substantially. For example, a jet engine may have one source at the jet nozzle exit and another source several nozzle diameters downstream from the jet nozzle exit. If a fixed array aperture is used to look at both sources, they will be seen in the noise source map data with differing resolution. The present disclosure provides a method that enables the two sources to be seen with the same resolution. By resizing the array 12 for each point in the source region that is being looked at, a noise source location map may be produced such that noise sources at any locations within the noise source region will be seen with the same resolution.

What is claimed is:

1. A system for an adaptable aperture planar array for maintaining source resolution as the array moves relative to a source comprising:
the source having a longitudinal axis;
a plurality of sensor elements each having a coordinate location within the array;
a first nested array defining a first aperture responsive to a first range of frequencies, the first aperture sized based on an angle between the array and the source, the first aperture including a first subset of sensor elements;
a second nested array defining a second aperture responsive to a second range of frequencies that is less than the first range of frequencies, the second aperture sized based on the angle between the array and the source, the second aperture including a second subset of sensor elements;
the first aperture and the second aperture change in size as the angle between the array and the source changes, which results in a change in the sensor elements within the first subset and the second subset so that the source resolution for the array remains substantially the same as the angle changes; and
a control module that resizes the first aperture and the second aperture based on the position of the array relative to the source, and changes the plurality of sensor elements associated with the first subset and the second subset based on the coordinate locations of the plurality of sensor elements within the resized first aperture and the resized second aperture to maintain the source resolution of the array.

2. The system of claim 1, further comprising:
a third nested array defining a third aperture responsive to a third range of frequencies that is less than the first range of frequencies and the second range of frequencies, the third aperture sized based on the angle between the array and the source, the third aperture including a third subset of sensor elements.

3. The system of claim 2, wherein the third subset of sensor elements includes at least one of the sensor elements associated with the first subset and at least one of the sensor elements associated with the second subset, and the second subset of sensor elements includes at least one of the sensor elements associated with the first subset.

4. The system of claim 2, wherein the third aperture is larger than the first aperture and the second aperture, and the second aperture is larger than the first aperture.

5. The system of claim 2, further comprising:
a fourth nested array defining a fourth aperture responsive to a fourth range of frequencies that is less than the first range of frequencies, the second range of frequencies and the third range of frequencies, the fourth aperture sized based on the angle between the array and the source, the fourth aperture larger than the third aperture, and the fourth aperture including a fourth subset of sensor elements that includes at least one of the sensor elements associated with the first subset, at least one of the sensor elements associated with the second subset and at least one of the sensor elements associated with the third subset.

6. The system of claim 1, wherein the source is a mobile platform.

7. The system of claim 1, wherein the first aperture and second aperture are sized based on a look angle measured between a line drawn from a center point of the array to a center point of the source and a normal to the center point of the array.

8. The system of claim 7, wherein the array is formed of a plurality of sensor elements, and each sensor element of the plurality of sensor elements has an x-coordinate and y-coordinate location within the array.

9. The system of claim 8, wherein each of the first aperture and the second aperture define a boundary for the first nested array and the second nested array, and the sensor element is selected to be within the first subset, second subset or combination thereof based on whether the x-coordinate and y-coordinate location of the sensor element is within the boundary defined by the first aperture of the first nested array, the second aperture of the second nested array or combination thereof.

10. The system of claim 9, wherein the boundary of the first aperture and the boundary of the second aperture are defined to include a plurality of locations having x and y coordinates, and the first aperture and the second aperture are resized as a function of the cosine of the look angle.

11. The system of claim 1, wherein the first aperture and the second aperture change in size as the array moves in a second direction parallel to the longitudinal axis of the source, which results in a change in the sensor elements within the first subset and the second subset so that the source resolution for the array remains substantially the same during the movement of the array in the second direction.

12. A method of maintaining source resolution for an adaptable aperture planar array movable relative to a source comprising:
providing a plurality of sensor elements that each include a coordinate location in the array;
determining a position of the array relative to the source;

computing a first nested array responsive to a first range of frequencies based on the position of the array, the first nested array including a first subset of the plurality of sensor elements;

computing a second nested array that is larger than the first nested array, the second nested array including a second subset of the plurality of sensor elements that includes at least one sensor element associated with the first subset;

acquiring data associated with the first range of frequencies with the first subset of the plurality of sensor elements;

acquiring data associated with the second range of frequencies with the second subset of the plurality of sensor elements;

determining that the position of the array relative to the source has changed;

recomputing the first nested array based on the changed position of the array; and recomputing the second nested array based on the changed position of the array, with the recomputing of the first nested array and the second nested array maintaining the source resolution for the array.

13. The method of claim 12, wherein determining a position of the array relative to the source further comprises:

receiving a user input that indicates a look angle measured between a line drawn from a center point of the array to a center point of the source and a normal to the array.

14. The method of claim 13, wherein computing the first nested array and second nested array further comprises:

determining a first aperture for the first nested array based on a look angle of zero degrees;

determining which of the plurality of sensor elements have coordinate locations within the first aperture to define the first subset;

determining a second aperture for the second nested array based on a look angle of zero degrees, with the second aperture being larger than the first aperture; and determining which of the plurality of sensor elements have coordinate locations within the second aperture to define the second subset.

15. The method of claim 14, wherein recomputing the first nested array and the second nested array when the position of the array relative to the source has changed further comprises:

recomputing the first aperture for the first nested array based on a function of the cosine of the look angle;

determining which of the plurality of sensor elements have coordinate locations within the recomputed first aperture;

associating at least one of the plurality of sensor elements within the recomputed first aperture to define a recomputed first subset;

recomputing the second aperture for the second nested array based on a function of the cosine of the look angle;

determining which of the plurality of sensor elements have coordinate locations within the recomputed second aperture; and associating at least one of the plurality of sensor elements within the recomputed second aperture to define a recomputed second subset.

16. The method of claim 15, further comprising:

acquiring data associated with the first range of frequencies with the recomputed first subset of the plurality of sensor elements when the position of the array relative to the source has changed; and acquiring data associated with the second range of frequencies with the recomputed second subset of the plurality of sensor elements when position of the array relative to the source has changed.

17. A system for an adaptable aperture planar array for maintaining source resolution as the array moves relative to a source comprising:

a source having a longitudinal axis;

a plurality of sensor elements each having a coordinate location within the array;

a first nested array defining a first aperture responsive to a first range of frequencies, the first aperture sized based on an angle between the array and the source, the first aperture including a first subset of the plurality of sensor elements, with each of the plurality of sensor elements within the first subset having coordinate locations within the first aperture;

a second nested array defining a second aperture responsive to a second range of frequencies that is less than the first range of frequencies, the second aperture larger than the first aperture and including a second subset of the plurality of sensor elements that includes at least one of the plurality of sensor elements associated with the first nested array, with each of the plurality of sensor elements within the second subset having coordinate locations within the second aperture;

a third nested array defining a third aperture responsive to a third range of frequencies that is less than the first range of frequencies and the second range of frequencies, the third aperture larger than the first aperture and the second aperture and including a third subset of the plurality of sensor elements that includes at least one of the plurality of sensor elements associated with the first subset and at least one of the plurality of sensor elements associated with the second subset, with each of the plurality of sensor elements within the third subset having coordinate locations within the third aperture; and a control module that resizes the first aperture, the second aperture and the third aperture based on the position of the array relative to the source, and changes the plurality of sensor elements associated with the first subset, the second subset and the third subset based on the coordinate locations of the plurality of sensor elements within the resized first aperture, second aperture and third aperture to maintain the source resolution of the array.

18. The system of claim 17, wherein the first aperture, second aperture and third aperture are changed in size in the x-direction by a factor of the cosine cubed of the angle, and are changed in size in the y-direction by a factor of the cosine of the angle.

19. The system of claim 17, wherein the first aperture, second aperture and third aperture are changed in size in the x-direction by a factor of the cosine of the angle and are changed in size in the y-direction by a factor of the cosine cubed of the angle.

20. The system of claim 17, wherein the array is at a fixed location and the first aperture, second aperture and third aperture are resized based on movement of the source relative to the array.

21. The system of claim 17, wherein the array is at a fixed location and the first aperture, second aperture and third aperture are resized based on the location in the source region around the source at which the array is looking.

* * * * *